(12) United States Patent
Rice et al.

(10) Patent No.: US 6,895,264 B2
(45) Date of Patent: May 17, 2005

(54) NON-INVASIVE PSYCHOPHYSICAL MEASUREMENT OF GLUCOSE USING PHOTODYNAMICS

(75) Inventors: Mark J. Rice, Jacksonville, FL (US); Joe W. Woods, Lexington, KY (US); Wilson Routt, Lexington, KY (US); Junli Ou, Lexington, KY (US)

(73) Assignee: Fovioptics Inc., Santa Clara, CA (US)

( * ) Notice: Subject to any disclaimer, the term of this patent is extended or adjusted under 35 U.S.C. 154(b) by 0 days.

(21) Appl. No.: 10/642,111

(22) Filed: Aug. 15, 2003

(65) Prior Publication Data

US 2004/0087843 A1 May 6, 2004

Related U.S. Application Data

(60) Provisional application No. 60/405,978, filed on Aug. 26, 2002.

(51) Int. Cl.[7] .................................................. A61B 5/00
(52) U.S. Cl. ........................................ 600/319; 600/316
(58) Field of Search ................................ 600/319, 316, 600/365

(56) References Cited

U.S. PATENT DOCUMENTS

| | | |
|---|---|---|
| 3,958,560 A | 5/1976 | March |
| 4,014,321 A | 3/1977 | March |
| 4,029,085 A | 6/1977 | DeWitt et al. |
| 4,194,217 A | 3/1980 | Van den Bosch |
| 4,249,825 A | 2/1981 | Shapiro |
| 4,305,398 A | 12/1981 | Sawa |
| 4,331,132 A | 5/1982 | Mukasa |
| 4,350,163 A | 9/1982 | Ford, Jr. et al. |
| 4,485,820 A | 12/1984 | Flower |
| 4,597,392 A | 7/1986 | Opitz et al. |
| 4,603,976 A | 8/1986 | Fetzer et al. |
| 4,750,830 A | 6/1988 | Lee |
| 4,757,381 A | 7/1988 | Cooper et al. |
| 4,758,081 A | 7/1988 | Barnes |
| 4,809,342 A | 2/1989 | Kappner et al. |
| 4,877,322 A | 10/1989 | Hill |
| 4,998,533 A | 3/1991 | Winkelman |
| 5,168,863 A | 12/1992 | Kurtzer |
| 5,201,908 A | 4/1993 | Jones |
| 5,204,532 A | 4/1993 | Rosenthal |

(Continued)

FOREIGN PATENT DOCUMENTS

| | | |
|---|---|---|
| DE | 4243142 A1 | 6/1994 |
| DE | 19741198 A1 | 6/1998 |

(Continued)

OTHER PUBLICATIONS

John B. Hickam, et al., "A Study of Retinal Venus Blood Oxygen Saturation in Human Subjects by Photographic Means,", Circulation, vol. XXVII, Mar. 1963, pp. 375–385.

(Continued)

Primary Examiner—Eric F. Winakur
Assistant Examiner—Matthew J. Kremer
(74) Attorney, Agent, or Firm—Wilson Sonsini Goodrich & Rosati (57) ABSTRACT

Blood glucose concentrations are measured by non-invasive methods and apparatus using visual pigment bleaching in conjunction with psychophysical methodologies. Bleaching light of selected wavelengths is projected through the pupil of the eye of an observer onto the fundus to bleach visual pigments in the eye. The observer's psychophysical response to a visual stimulus is then measured to obtain information regarding the rate of regeneration of the visual pigments. From the rate of pigment regeneration, blood glucose concentrations are measured accurately. The psychophysical methodologies that may be used with the invention include visual acuity tests and color-matching tests.

22 Claims, 10 Drawing Sheets

U.S. PATENT DOCUMENTS

| | | |
|---|---|---|
| 5,209,231 A | 5/1993 | Cote et al. |
| 5,219,400 A | 6/1993 | Jacot et al. |
| 5,222,495 A | 6/1993 | Clarke et al. |
| 5,222,496 A | 6/1993 | Clarke et al. |
| 5,243,983 A | 9/1993 | Tarr et al. |
| 5,259,382 A | 11/1993 | Kronberg |
| 5,262,304 A | 11/1993 | Taniguchi |
| 5,277,181 A | 1/1994 | Mendelson et al. |
| 5,297,554 A | 3/1994 | Glynn et al. |
| 5,318,022 A | 6/1994 | Taboada et al. |
| 5,353,790 A | 10/1994 | Jacques et al. |
| 5,359,991 A | 11/1994 | Takahashi et al. |
| 5,363,838 A | 11/1994 | George |
| 5,363,843 A | 11/1994 | Daneshvar |
| 5,377,674 A | 1/1995 | Kuestner |
| 5,398,681 A | 3/1995 | Kupershmidt |
| 5,406,939 A | 4/1995 | Bala |
| 5,424,545 A | 6/1995 | Block et al. |
| 5,433,197 A | 7/1995 | Stark |
| 5,434,412 A | 7/1995 | Sodickson et al. |
| 5,448,992 A | 9/1995 | Kupershmidt |
| 5,452,723 A | 9/1995 | Wu et al. |
| 5,487,384 A | 1/1996 | Lee |
| 5,507,288 A | 4/1996 | Bocker et al. |
| 5,535,743 A | 7/1996 | Backhaus et al. |
| 5,551,422 A | 9/1996 | Simonsen et al. |
| 5,553,617 A | 9/1996 | Barkenhagen |
| 5,560,356 A | 10/1996 | Peyman |
| 5,576,544 A | 11/1996 | Rosenthal |
| 5,582,168 A | 12/1996 | Samuels et al. |
| 5,598,842 A | 2/1997 | Ishihara et al. |
| 5,627,895 A | 5/1997 | Owaki |
| 5,668,621 A | 9/1997 | Nanjo |
| 5,671,301 A | 9/1997 | Kupershmidt |
| 5,676,143 A | 10/1997 | Simonsen et al. |
| 5,692,503 A | 12/1997 | Kuenstner |
| 5,713,353 A * | 2/1998 | Castano ............... 600/319 |
| 5,722,398 A | 3/1998 | Ishihara et al. |
| 5,743,849 A | 4/1998 | Rice et al. |
| 5,770,454 A | 6/1998 | Essenpreis et al. |
| 5,771,891 A | 6/1998 | Gozani |
| 5,776,060 A | 7/1998 | Smith et al. |
| 5,784,162 A | 7/1998 | Cabib et al. |
| 5,788,632 A | 8/1998 | Pezzaniti et al. |
| 5,792,050 A | 8/1998 | Alam et al. |
| 5,818,048 A | 10/1998 | Sodickson et al. |
| 5,820,547 A | 10/1998 | Strobl et al. |
| 5,820,557 A * | 10/1998 | Hattori et al. ........... 600/319 |
| 5,835,215 A | 11/1998 | Toida et al. |
| 5,840,035 A | 11/1998 | Heusmann et al. |
| 5,893,364 A | 4/1999 | Haar et al. |
| 5,896,198 A | 4/1999 | Chou et al. |
| 5,919,132 A | 7/1999 | Faubert et al. |
| 5,935,076 A | 8/1999 | Smith et al. |
| 6,011,986 A | 1/2000 | Diab et al. |
| 6,039,697 A | 3/2000 | Wilke et al. |
| 6,113,537 A | 9/2000 | Castano |
| 6,120,460 A | 9/2000 | Abreu |
| 6,152,875 A | 11/2000 | Hakamata |
| 6,181,957 B1 | 1/2001 | Lambert et al. |
| 6,188,477 B1 | 2/2001 | Pu et al. |
| 6,213,943 B1 | 4/2001 | Abreu |
| 6,246,893 B1 | 6/2001 | Gobeli |
| 6,305,804 B1 | 10/2001 | Rice et al. |
| 6,312,393 B1 | 11/2001 | Abreu |
| 6,327,037 B1 | 12/2001 | Chou et al. |
| 6,370,407 B1 | 4/2002 | Kroeger et al. |
| 6,423,001 B1 | 7/2002 | Abreu |
| 6,424,850 B1 | 7/2002 | Lambert et al. |
| 6,442,410 B1 | 8/2002 | Steffes |
| 6,477,394 B2 | 11/2002 | Rice et al. |
| 6,494,576 B1 | 12/2002 | L'Esperance, Jr. |
| 6,537,207 B1 | 3/2003 | Rice et al. |
| 6,544,193 B2 | 4/2003 | Abreu |
| 6,650,915 B2 * | 11/2003 | Routt et al. ............... 600/319 |
| 6,681,127 B2 | 1/2004 | March |
| 6,704,588 B2 | 3/2004 | Ansari et al. |
| 2001/0031914 A1 | 10/2001 | Gobeli et al. |
| 2001/0034500 A1 | 10/2001 | March |
| 2002/0007113 A1 | 1/2002 | March et al. |
| 2002/0049374 A1 | 4/2002 | Abreu |
| 2002/0049389 A1 | 4/2002 | Abreu |
| 2002/0072658 A1 | 6/2002 | Rice et al. |
| 2003/0008407 A1 | 1/2003 | Fu et al. |
| 2003/0045783 A1 | 3/2003 | March et al. |
| 2003/0050544 A1 | 3/2003 | Routt et al. |
| 2003/0076508 A1 | 4/2003 | Cornsweet |
| 2003/0139687 A1 | 7/2003 | Abreu |
| 2003/0225321 A1 | 12/2003 | Cote et al. |
| 2003/0233036 A1 | 12/2003 | Ansari et al. |
| 2004/0087843 A1 | 5/2004 | Rice et al. |
| 2004/0087844 A1 | 5/2004 | Yen |
| 2004/0111018 A1 | 6/2004 | Isenberg et al. |
| 2004/0133093 A1 | 7/2004 | Glynn |
| 2004/0138539 A1 | 7/2004 | Jay et al. |
| 2004/0147820 A1 | 7/2004 | Routt et al. |
| 2004/0152963 A1 | 8/2004 | March |
| 2004/0220457 A1 | 11/2004 | Burd et al. |
| 2004/0220458 A1 | 11/2004 | Burd et al. |

FOREIGN PATENT DOCUMENTS

| | | |
|---|---|---|
| EP | 0122961 A2 | 10/1984 |
| EP | 0236023 A2 | 9/1987 |
| EP | 0471725 B1 | 12/1995 |
| EP | 0722692 A1 | 7/1996 |
| EP | 0561872 B1 | 8/1996 |
| EP | 0589191 B1 | 3/1997 |
| EP | 0603658 B1 | 2/1999 |
| EP | 0686372 B1 | 1/2001 |
| EP | 0807812 B1 | 5/2002 |
| EP | 0792619 B1 | 1/2004 |
| TW | 445373 B | 7/2001 |
| WO | WO88/00447 | 1/1988 |
| WO | WO 92/07511 A1 | 5/1992 |
| WO | WO92/17765 | 10/1992 |
| WO | WO 93/01745 A1 | 2/1993 |
| WO | WO93/07801 | 4/1993 |
| WO | WO 95/24152 A1 | 9/1995 |
| WO | WO97/15229 | 5/1997 |
| WO | WO 97/34521 A1 | 9/1997 |
| WO | WO 97/39686 A1 | 10/1997 |
| WO | WO92/07278 | 2/1999 |
| WO | WO 99/18848 A1 | 4/1999 |
| WO | WO 00/02479 A1 | 1/2000 |
| WO | WO 00/16692 A1 | 3/2000 |
| WO | WO 00/59366 A2 | 10/2000 |
| WO | WO 00/60350 A2 | 10/2000 |
| WO | WO 01/06918 A1 | 2/2001 |
| WO | WO 01/22061 A1 | 3/2001 |
| WO | WO 01/022871 A1 | 4/2001 |
| WO | WO 01/78589 A1 | 10/2001 |
| WO | WO 02/26119 A2 | 4/2002 |
| WO | WO 02/060321 A2 | 8/2002 |
| WO | WO 02/069789 A1 | 9/2002 |
| WO | WO 02/071932 A1 | 9/2002 |
| WO | WO 02/087429 A1 | 11/2002 |
| WO | WO 03/012486 A2 | 2/2003 |
| WO | WO 03/025562 A2 | 3/2003 |
| WO | WO 03/037174 A1 | 5/2003 |
| WO | WO 03/087775 A2 | 10/2003 |
| WO | WO 2004/012576 A2 | 2/2004 |
| WO | WO 2004/041348 A2 | 5/2004 |
| WO | WO 2004/060154 A1 | 7/2004 |
| WO | WO 2004/071287 A1 | 8/2004 |
| WO | WO 2004/099824 A2 | 11/2004 |

OTHER PUBLICATIONS

S. Futterman, et al., "Metabolism of Glucose and Reduction of Retinaldehyde in Retinal Photoreceptors," J. of Neural Chemistry, vol. 17, 1970, pp. 149–156.

Michael A. Cusanovich, "Kinetics and Mechanism of Rhodopsin Regeneration with 11–cis–Retinal," Methods in Enzymology, vol. 81, 1982, pp. 443–447.

Toyowo Akimoto, "Light–Induced Transmission Changes in Isolated Vertebrate Retinas," Vision Research, vol. 22, 1982, pp. 1093–1096.

Joseph D. Kokozo, et al., "Factors Affecting the Regeneration of Rhodopsin in the Isolated Amphibian Retina," Vision Research, vol. 27, No. 7, 1987, pp. 1085–1091.

Shu–Chan Hsu, et al., "Glycolytic Enzymes and a Glut–1 Glucose Transporter in the Outer Segments of Rod and Cone Photoreceptor Cells," J. of Biological Chemistry, vol. 266, No. 32, Nov. 15, 1991, pp. 21745–21752.

John C. Saari, "The Biochemistry of Sensory Transduction in Vertebrate Photoreceptors," Chapter 14, Adler's Phsyiology of the Eye, Ninth Edition, Mosby Yearbook, Publishers, 1992, pp. 460–484.

Sanford E. Ostroy, et al., "Extracellular Glucose Dependence of Rhodopsin Regeneration in the Excised Mouse Eye," Exp. Eye Research, vol. 55, 1992, pp. 419–423.

John H. Parkes, et al., "Effect of Photoregeneration on the Calculation of the Amount of Rhodopsin Bleached by Small Flashes," Biophysical Journal, vol. 66, Jan. 1994, pp. 60–88.

Shu–Chan Hsu, et al., "Glucose Metabolism in Photoreceptor Outer Segments," J. of Biological Chemistry, vol. 269, No. 7, Jul. 8, 1994, pp. 17954–17969.

Sanford E. Ostroy, et al., "Decreased Rhodopsin in Regeneration in Diabetic Mouse Eyes," Investigative Ophthalmology & Visual Science, vol. 35, No. 11, Oct. 1994, pp. 3905–3909.

Maria K. Van den Enden, et al., "Elevated Glucose Levels Increase Retinal Clycolysis and Sorbitol Pathway Metabolism," Investigative Ophthalmology & Visual Science, vol. 36, No. 8, Jul. 1995, pp. 1675–1685.

Barry S. Winkler, et al., "Glucose Dependence of Glycolysis, Hexose Monophosphate Shunt Activity, Energy Status, and the Polyol Pathway in Retinas Isolated from Normal (Non–Diabetic) Rats," Investigative Ophthalmology & Visual Science, vol. 38, No. 1, Jan. 1997, pp. 62–71.

L. Wang, et al., "Glucose Metabolism in Pig Outer Retina in Light and Darkness," Acta Physiol Scand, vol. 160, 1997, pp. 75–81.

J. Zubay, Vision Chapter 29, Biochemistry, Fourth Edition, Wm. C. Brown, publishers, 1998, pp. 717–729.

Sanford E. Ostroy, "Altered Rhodopsin Regeneration in Diabetic Mice Caused by Acid Conditions Within the Rod Receptors," Current Eye Research, vol. 17, 1998, pp. 979–985.

Begg et al, "Photostress Recovery Time in Type 1 Diabetics", Invest. Opth. Vis. Science, vol. 22 (suppl): 68 (1982).

Blackman et al., "Hypoglycemic thresholds for cognitive dysfunction in IDDM", Diabetes, vol. 41, pp. 392–399 (1992).

Burns, S. et al., "A Psychophysical Technique for Measuring Cone Photopigment Bleaching", Invest. Ophthal. Vis. Science, vol. 28, pp. 711–717 (1987).

Burns, S. et al., "Color Matching at High Illuminances: the color–match–area effect and photopigment bleaching", J. Opt. Soc. Am., vol. 2, p. 698 (1985).

Burns, S. et al., "Color Matching at High Illuminances: photopigment optical density and pupil entry", J. Opt. Soc. Am., vol. 10, pp. 221–230 (1993).

Castano, J. et al., "Blood Glucose Dependence of Visual Flicker Threshold", Diabetes Technology & Therapeutics, vol. 2, No. 1, (2000).

Chilaris GA: Recovery Time After Macular Illumination, Am J Ophthal 53:311–314, 1962.

Cocozza JD, Ostroy SE: Factors Affecting the Regeneration of Rhodopsin in the Isolated Amphibian Retina, Vision Research 27: 1085–1091. 1987.

Cusanovich, M. A., "Kinetics and Mechanism of Rhodopsin Regeneration with 11–cis–Retinal", Methods in Enzymology, vol. 81, pp. 443–447 (1982).

Elsner, et al., "Cone Pigment Bleaching Abnormalities in Diabetes", Invest. Ophthal. Vis. Science, vol. 28, pp. 718–724 (1987).

Ewing, F. et al., "Seeing Beyond Retinopathy in Diabetes: Electrophysical and Physchological Abnormalities and Alterations of Vision", Endocrine Reviews, vol. 19(4), pp. 462–476 (1998).

Futteman, S. et al., "Metabolism of Glucose and Reduction of Retinaldehyde in Retinal Receptors", J. Neurochemistry, vol. 17, pp. 149–156 (1970).

Glaser et al. "The Photostress Recovery Time in the Clinical Assessment of Visual Function", Am . J. Ophthal., vol. 83, p. 255 (1977).

Hollins, M. et al., "Dark Adaptation and Visual Pigment Regeneration in Human Cones", J. Gen. Phys., vol. 62, p. 430 (1973).

Hsu, S. C. et al., "Glucose Metabolism in Photoreceptor Outer Segments", J. of Biol. Chem., vol. 269, pp. 17954–17969 (1970).

Mahroo, O. et al., "Recovery of the human photopic electroretinogram after bleaching exposures: estimation of pigment regeneration kinetics", J. Physiol., vol. 554.2, pp. 417–437 (2003).

Ostroy, S.E., "Extracellular Glucose Dependence of Rhodopsin Regeneration in the Excised Mouse Eye", Exp. Eye Research, vol. 55, pp. 419–423 (1992).

Ostroy, S.E., et al., "Decreased Rhodopsin Regeneration in Diabetic Mouse Eyes", Invest. Ophth. and Visual Science, vol. 35, pp. 3905–3909 (1994).

Ostroy, S.E. et al., "Altered Rhodopsin Regeneration in Diabetic Mice Caused by Acid Conditions Within Rod Receptors", Current Eye Res., vol. 17, pp. 979–985 (1998).

Sandburg et al. "Visual Recovery & Pigment Regeneration After Bleach", Invest. Ophthal. Vis. Science, vol. 40(10), pp. 2457–61 (1999).

Saari, J. C., "Biochemistry of Visual Pigment; the Friedenwald Lecture", Invest. Ophthal Vis Science 41:337–348, 2000.

Van Den Enden, M. K. et al., "Elevated Glucose Levels Increase Retinal Glycolysis and Sorbitol Pathway Metabolism", Invest. Ophth. and Visual Science, vol. 36, pp. 1675–1685 (1995).

Volbrecth et al., "Diabetic Short–Wavelength Sensitivity: Variations With Induced Changes in Blood Glucose Level", Invest. Ophthal. Vis. Science, vol. 35, pp. 1243–1246 (1994).

Wang, L. et al., "Glucose Metabolism in Pig Outer Retina in Light and Darkness", Acta Physiol. Scand., vol. 160, pp. 75–81 (1997).

Wyszecki, G., "Color Matching at Moderate to High Levels of Retinal Illuminance: A Pilot Study", Vision Res., vol. 18, pp. 341–346 (1978).

Zubay, J., Vision, Chapter 29, Biochemistry, Fourth Edition (1998) Wm. C. Brown, Publishers.

* cited by examiner

Fig. 6
Visual Acuity Following Repeated Bleachings
(M.R. Left Eye)

Visual Acuity Following Repeated Bleachings
(M.R. Right Eye)

NON-INVASIVE PSYCHOPHYSICAL MEASUREMENT OF GLUCOSE USING PHOTODYNAMICS

CROSS-REFERENCE TO RELATED APPLICATION

This application claims the benefit of provisional application No. 60/405,978, filed Aug. 26, 2002, the disclosure of which is incorporated by reference.

FIELD OF THE INVENTION

This invention pertains to the field of non-invasive in vivo measurement of blood glucose.

BACKGROUND OF THE INVENTION

The measurement of blood glucose by diabetic patients has traditionally required the drawing of a blood sample for in vitro analysis. The blood sampling is usually drawn by the patient as a finger puncture. The need to draw blood for analysis is undesirable for a number of reasons, including discomfort to the patient, the time required for medical personal to draw and handle the samples, the high cost of testing supplies, and the potential risk of spread of disease through punctures of the skin.

Many of the estimated three million Type 1 (juvenile) diabetics in the United States are asked to test their blood glucose six times or more per day in order to adjust their insulin doses for tighter control of their blood glucose. As a result of the discomfort, many of these patients do not test as often as is recommended by their physician, with the consequence of poor blood glucose control. This poor control has been shown to result in increased complications from this disease. Among these complications are blindness, heart disease, kidney disease, ischemic limb disease, and stroke. In addition, there is recent evidence that Type 2 (adult-onset) diabetics (numbering over 10 million in the United States) may reduce their incidence of diabetes-related complications by more tightly controlling their blood glucose. Accordingly, these patients may be asked to test their blood glucose as often as the Type 1 diabetic patients.

It would thus be desirable to obtain fast and reliable measurements of blood glucose concentrations through simple, non-invasive testing. Prior efforts have been unsuccessful in the quest for a sufficiently accurate, non-invasive blood glucose measurement. Many of these efforts have involved the passage of light waves through solid tissues such as the fingertip or the ear lobe, with subsequent measurement of the molecular absorption spectrum of glucose. These efforts have been largely unsuccessful primarily due to the variability of absorption and scatter of the electromagnetic energy in the tissues. Other groups have attempted blood glucose measurements in body fluids such as the anterior chamber, tears, and interstitial fluids. To date, these efforts have met with only limited success.

Thus a need exists for a simple, painless, non-invasive method for determining the concentration of glucose in a patient's blood.

SUMMARY OF THE INVENTION

The present invention provides a method and apparatus for determining the concentration of glucose in a patient's blood using psychophysical techniques. The invention combines the accuracy of in vitro laboratory testing of blood glucose with the advantages of a rapidly repeatable non-invasive technology. The invention utilizes an instrument that allows non-invasive determination of blood glucose concentration by the psychophysical measurement of the regeneration rate of the retinal visual pigments, including both rod rhodopsin and cone pigments. The regeneration rate of the visual pigments is dependent upon blood glucose concentration, therefore by measuring the regeneration rate of the visual pigments, the blood glucose concentration can be accurately determined.

The method of the invention includes the steps of: (1) bleaching the visual pigments in the retina of an observer's eye with a bleaching light, (2) conducting a psychophysical test that measures the observer's psychophysical response to a visual stimulus, and (3) analyzing the psychophysical response to determine the glucose concentration in the observer's blood.

The bleaching process involves exposing a particular region of an observer's retina to a bleaching light of selected wavelengths to bleach the visual pigments in the retina. Bleaching of the visual pigment refers to the illumination of the rods and cones of the retina by light energy that is capable of breaking down the visual pigment and initiating the visual cycle (pigment regeneration). The term "bleaching" was coined in the nineteenth century after the discovery that the retina underwent an actual color change upon the light striking the retina. As the pigment is regenerated, the color of the retina is returned to the unbleached state. For the purposes of this invention, a bleaching light may be any light that is capable of bleaching visual pigments, including rod and/or cone pigments.

The present invention is based, at least in part, on the surprising and unexpected discovery that the concentration of a patient's blood glucose can be accurately determined from calculations of visual pigment regeneration rates obtained by psychophysical tests. Psychophysical testing is the study of the relationship between physical stimuli, in this case visual stimuli, and the perception of the stimuli by an observer. Psychophysical measurements may be used to monitor an observer's response to stimuli, and are particularly useful in determining thresholds of perception. The threshold is the point at which an observer can just detect (or just not detect) a stimulus.

Several well-known psychophysical methods are capable of accurately measuring the regeneration rates of the visual pigments. These psychophysical methods of measuring visual pigment regeneration include but are not limited to contrast testing, such as color-matching during varying levels of retinal bleaching, as well as the return of visual acuity following bleaching. Return of visual acuity can be measured by monitoring the recovery time from a retinal bleach to the point in time when an observer recovers the ability to see either a flickering light or a discrete image. Other well-known psychophysical tests that may be used in conjunction with the invention include color vision tests, photostress tests, and perimetry (visual fields tests).

Further objects, features, and advantages of the invention will be apparent from the following detailed description when taken in conjunction with the accompanying drawings.

DETAILED DESCRIPTION OF THE INVENTION

In the present invention, psychophysical testing is used to non-invasively measure the regeneration rate of the visual pigment following a pigment bleach. By measuring the regeneration rates, the blood glucose concentration of a patient can be accurately determined.

Traditionally, rhodopsin and cone pigment regeneration have been measured through the use of retinal densitometry. Retinal densitometry is a non-invasive technique based on a comparison between the light reflected from a bleached retina and the light reflected from the retina following complete dark adaptation. By measuring and comparing light at a series of wavelengths, retinal densitometry can be used to measure the rate of pigment regeneration. Although this method has been proven to be an accurate measure of regeneration, it is potentially a difficult and costly method of measuring the process of visual pigment regeneration. Several difficulties arise with densitometry including the small signal to noise ratio that exists secondary to the minute amount of light that is emitted from the eye compared to the large amount of illuminating light entering the pupil. In addition, it is difficult to eliminate the stray light that is generated from the corneal reflection of the illuminating light. Therefore, it is desirable to measure cone pigment regeneration, and thus the blood glucose concentration, with an alternative method. In the present invention, retinal visual pigment regeneration is measured accurately with psychophysical methodology.

The visual pigments in an eye are located in the rods and cones within an observer's retina. The rods and cones of the retina are arranged in specific locations in the back of the eye. The cones, which provide central and color vision, are located with their greatest density in the area of the fovea centralis in the retina. The fovea centralis covers a circular area with a diameter of about 1.5 mm, with a subtended angle of about 3 degrees. The rods are distributed throughout the more peripheral portions of the retina and contribute to dim vision.

Rhodopsin and cone pigments are the visual pigments contained in the outer portions of the rods and cones of the retina, respectively. As the visual pigment absorbs light, it breaks down into intermediate molecular forms and initiates a signal that proceeds down a tract of nerve tissue to the brain, allowing for the sensation of sight. The outer segments of the rods and cones contain large amounts of these pigments, stacked in layers lying perpendicular to the light incoming through the pupil. There are two types of visual pigment, with a slight difference between the rhodopsin in the rods (that allow for dim vision) and the cone pigments (that allow for central and color vision). Rhodopsin absorbs light energy in a broad band of the electromagnetic spectrum centered at 500 nm, whereas there are three different cone pigments having broad overlapping absorption bands peaking at 430, 550, and 585 nm. In accordance with the present invention, blood glucose concentration may be obtained from the rate of regeneration of either cone pigments or rod pigments, such as rod rhodopsin. In various embodiments, it is preferable to monitor the regeneration rate of the cone pigments because those pigments regenerate faster than the rhodopsin located in the rods. However, the regeneration rates of the rod pigments may be used for the measurement of the blood glucose in accordance with the invention.

The following is a description of the biochemistry of rhodopsin, although the biochemistry of the cone pigments is thought to be very similar. This description is intended merely to assist the reader in understanding the general nature of the invention and is not intended to bind the inventors to any particular theory of operation with regard to the invention. Rhodopsin consists of 11-cis-retinal and the protein opsin, which is tightly bound in the outer segment of the rods. 11-cis-retinal is the photoreactive portion of rhodopsin, which is converted to all-trans-retinal when a photon of light in the active absorption band strikes the molecule. This process goes through a sequence of chemical reactions as 11-cis-retinal isomerizes to all-trans-retinal. During this series of chemical steps, the nerve fiber, which is attached to that particular rod or cone, undergoes a stimulus that is ultimately perceived in the brain as a visual signal.

Following the breakdown of 11-cis-retinal to all-trans-retinal, the 11-cis-retinal is regenerated by a series of steps that result in 11-cis-retinal being recombined with opsin protein in the cell or disk membrane. A critical step in this regeneration pathway is the reduction of all-trans-retinal to all-trans-retinol, which requires NADPH as the direct reduction energy source. In a series of experiments, Futterman et al. have proven that glucose, via the pentose phosphate shunt (PPS), provides virtually all of the energy required to generate the NADPH needed for this critical reaction. S. Futterman, et al., "Metabolism of Glucose and Reduction of Retinaldehyde Retinal Receptors," J. Neurochemistry, 1970, 17, pp. 149–156. Without glucose or its immediate metabolites, no NADPH is formed and rhodopsin cannot regenerate.

There is strong evidence that glucose is a very important energy substrate for the integrity and function of the retinal outer segments. It has been known for over thirty years that glucose and glycolysis (the metabolism of glucose) are important in maintaining the structure and function of the retinal outer segments. More recently, it has been discovered that one of the major proteins contained in the retinal outer segments is glyceraldehyde-3-phosphate dehydrogenase, an important enzyme in glucose metabolism. This points to the importance of glucose as the energy source for the metabolism in the retinal outer segments, which has as its primary function the maintenance of high concentrations of rhodopsin.

It has been shown that the extracellular glucose concentration has a major effect on rhodopsin regeneration. S. E. Ostroy, et al., "Extracellular Glucose Dependence of Rhodopsin Regeneration in the Excised Mouse Eye," Exp. Eye Research, 1992, 55, pp. 419–423. This data reveals that increasing rhodopsin regeneration is associated with increasing extracellular concentrations of glucose. Extracellular glucose concentration is the primary energy driver for rhodopsin regeneration. The present invention utilizes this principle to measure extracellular glucose concentration.

Device Description

Figure 1:
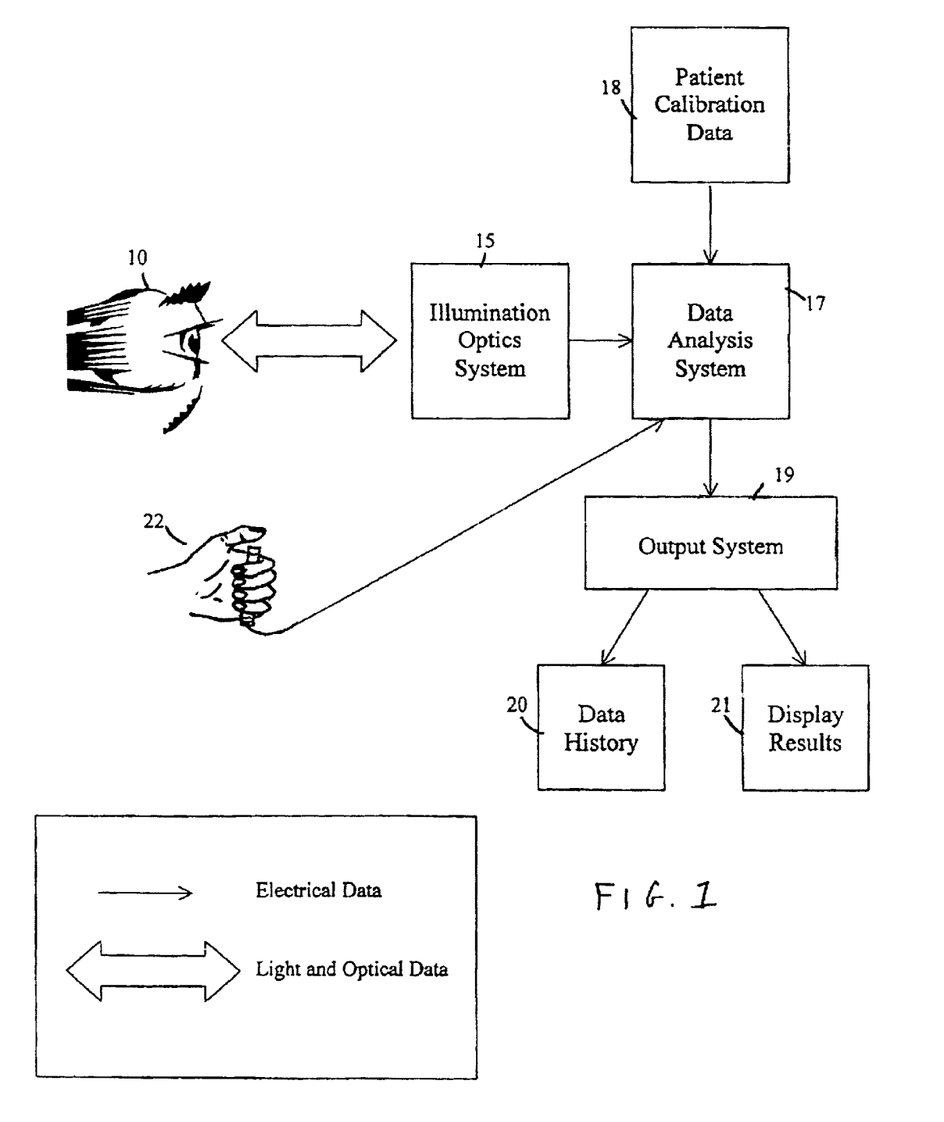
FIG. 1 is a schematic diagram of an apparatus for measurement of the concentration of blood glucose using visual acuity testing.
Figure 9:
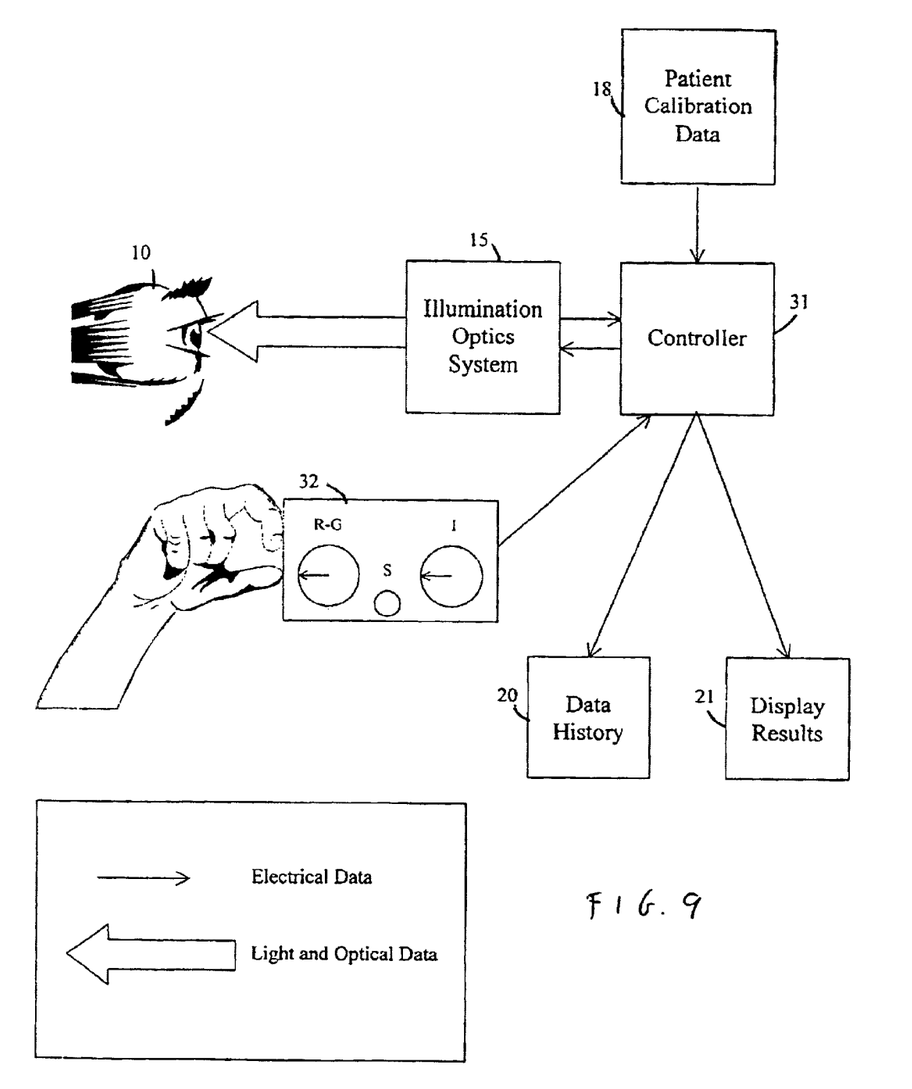
FIG. 9 is a schematic diagram of the preferred embodiment of the color-matching optical system.

With reference to the drawings, FIG. 1 and FIG. 9 illustrate two exemplary glucose analysis apparatus in accordance with the invention in conjunction with the eye of a patient, shown illustratively at 10 in the figures. The glucose analysis apparatus include an illumination and optics system 15 comprised of a light source and lens system for projecting bleaching light onto the fundus, directly through the pupil. The lenses preferably include a final lens, which can be positioned close to the cornea of the eye, providing a 5 to 15 degree conical illumination of the retina. This lens system floods the fovea with illuminating (bleaching) light. Such lens systems are of conventional design and are well-known.

Figure 3:
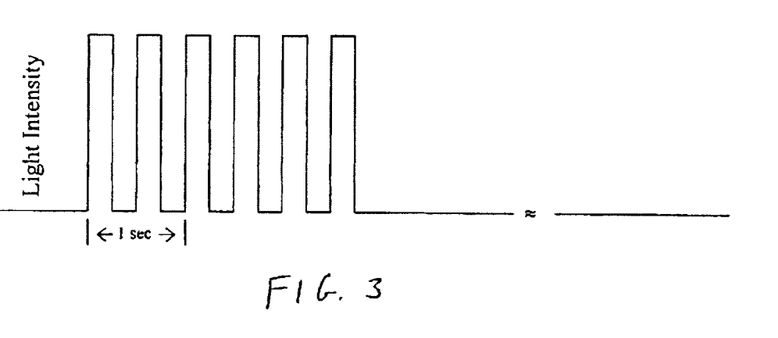
FIG. 3 is an illustrative diagram of one example of the bleaching signal from the illumination source.

The bleaching light may be any light containing wavelengths that are suitable for bleaching visual pigments in the retina of an observer. In various embodiments the bleaching light from the illumination and optics system 15 may include a time varying (modulated) light amplitude, with one example of a bleaching light amplitude as a function of time as illustrated in FIG. 3. The bleaching light may be one pulse of light or a number of pulses of light. The time varying signal is preferably a pulsed signal as shown in FIG. 3. This light may be used to bleach the cone or rod pigments of the retina. The wavelength range of the bleaching light preferably matches the active range of the visual pigment molecules. The wavelength of the bleaching light is preferably in the range of 500 nm to 650 nm, e.g., 595 nm, for analysis of glucose, although other wavelength ranges may be utilized as appropriate. Bleaching light may be provided by various light sources, for example, a light emitting diode (LED), a xenon light, or a halogen light source. LED illumination is preferred because of the ease of varying the intensity of the light from the LED by varying the input power to the LED. Alternatively, steady state sources may be used with light modulators to provide the appropriate time varying illumination.

The patient being tested may be directed to look directly at the light source, and by centering the field of view on the incoming light, the appropriate area of the fundus (fovea centralis) will be illuminated. To steady the bleached (tested) eye, the contra-lateral eye may be used for fixation. A binocular optics system may be employed wherein the non-tested eye is fixated on a target (e.g., a crosshair) during the entire testing sequence of bleaching and recognition of the visual stimulus. This fixation keeps the tested eye fixated during bleaching and recognition, a time period in which the tested eye may wander due to a lack of any visual stimuli. Alternatively, a single eye may be used for the bleaching and fixation. This is accomplished by having a dim rim of light maintained throughout the testing period as a fixation method. Although the invention may be carried out with a dilated eye pupil, it is an advantage of the present invention that the testing can be carried out without requiring dilation of the pupil for speed of measurement and patient convenience.

Once the pigments have been bleached, the rate of regeneration of the visual pigments is measured by psychophysical methodology. There is a period of time (typically measured in seconds) following retinal bleaching during which an observer's perception of a visual stimulus will be affected by the bleaching of the observer's visual pigments. The effects of the bleaching and the manner of measuring the effects (i.e. the psychophysical methodologies) may take a variety forms depending on the nature of the visual stimulus. For example, the effect of the bleaching on visual acuity may be measured by monitoring the time it takes for the observer to be able to identify an illuminated target, which may be a flickering target, after pigment bleaching. Alternatively, the effect of pigment bleaching on an observer's ability to discern a color contrast may be measured by asking an observer to identify a color and intensity match between a given colored field and a variety of possible matching fields at different bleaching levels.

The data for visual pigment regeneration rates, as measured by the observers perception of a given visual stimulus, may then be correlated with blood glucose concentration measurements. This data, along with patient calibration data 18 may, for example, be utilized in a neural network simulation carried out by computer. Calibration data may be obtained in advance by measuring a given patient's response to or perception of a given stimulus while simultaneously measuring the patient's blood glucose level using conventional blood glucose measuring techniques. Neural network simulators are well known. Exemplary neural network analysis tools that may be used in one embodiment of the invention are contained in the MATLAB™ language and in the Neural Network Toolbox of MATLAB™ version 12.1. The neural network iteratively generates weights and biases, which optimally represent, for the network structure used, the relationship between visual pigment regeneration rates and blood glucose values determined by the usual methods. The desired relationship may be amenable, alternatively, to development as a look-up table, regression model, or other algorithm carried out in a data analysis system 17, e.g., a special purpose computer or an appropriately programmed personal computer, work station, etc.

The relationship between the visual pigment regeneration rates measured using the apparatus of the invention and measurements made on blood samples taken from the individual patient may change over a period of time. The patient calibration data in the data storage 18 may be combined with an algorithm carried out in a data analysis system 17 to predict the specific patient's blood glucose concentration, and the calibration data may be periodically updated. This algorithm may be implemented in an integrated electronic chip, which may be contained in the device for providing the transfer function between the measured visual pigment regeneration rates and the blood glucose concentration. There may be patient-to-patient variability and each device may be calibrated for an individual patient on a regular interval (e.g., every three to six months). This may be necessary as the changing state of each patient's disease (diabetes mellitus) affects retinal biochemistry and thus, influences the regeneration rates of the visual pigment. The intermittent calibration of the device is useful in patient care as it facilitates the diabetic patient returning to the healthcare provider for follow-up of their disease. The device may be equipped with a method of limiting the number of tests, so that patient follow-up will be required to reactivate the device.

The results of the calculated blood glucose concentration from the data analysis system 17 are provided to an output system 19 for storage, display or communication. By storing the data for a given observer's blood glucose concentrations over a period of time, a data history for that observer may be developed. A readout of the glucose concentration history from data history storage 20 may be obtained by the health care provider at convenient intervals. The blood glucose concentration may be directed from the output system 19 to a display 21 to provide for patient observation. This display 21 will be preferably by an LCD screen located on the device as depicted as 21 in FIG. 1, FIG. 7 and FIG. 9. The observer (patient) can provide a response during testing, using a switch 22 or other suitable device.

Two exemplary embodiments of the invention are described herein. Although this description specifically describes these two general embodiments, this does not limit the invention to only these two embodiments, but includes any embodiment that uses psychophysical methodology to measure the visual pigment regeneration rate and thus allow the determination of blood glucose concentration. These embodiments will now be described. The first embodiment utilizes visual acuity tests as the psychophysical methodology. This embodiment comprises bleaching the visual pigments in an observer's retina with a bleaching light, or a series of bleaching lights, followed by measuring the return of visual acuity as measured by the observer's ability to recognize an illuminated or flickering target. The second embodiment utilizes color-matching tests as the psychophysical methodology. This embodiment comprises a method of color-matching during varying bleaching levels in order to measure the blood glucose concentrations.

Figure 2:
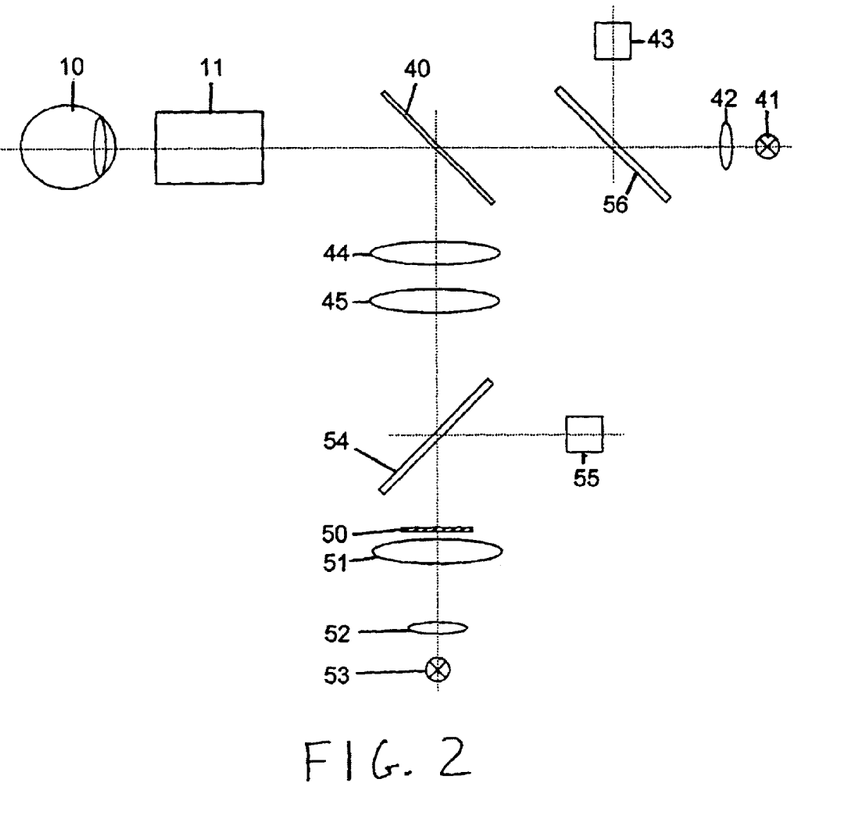
FIG. 2 is a schematic diagram of the preferred embodiment of the illumination and optical system of the apparatus of FIG. 1.

FIG. 2 shows a schematic diagram of the illumination and optical system 15, used in conjunction with the first embodiment of the invention. The optical layout of the system includes a target 50 that is illuminated by a first LED 53 and a high illumination bleaching source LED 41. The LED 41 is preferably a 595 nm yellow light source. The light from the LED 41 is collimated by an aspheric lens 42 and then passed through a glass plate 56 and a pellicle beam splitter 40 (i.e., 92/8), and then is gathered by an eyepiece lens combination 11 and enters the patient's eye 10. All light is presented to the patient's eye in Maxwellian view. A target image is presented to the eye 10 via a right angle path illuminated by the first LED 53 at e.g., 595 nm. Light from the LED 53 is focused by an aspheric lens 52 (e.g., 5.21 mm focal length) to produce an image of the light generating LED element at the lens 51 (e.g., 275 mm PCX or achromat). The target 50 is positioned to produce a target image at the input of the eyepiece lens 11. Two achromatic lenses 44 and 45 (e.g., 100 mm and 275 mm focal lengths) are utilized to image the target at the eyepiece 11 (e.g., 32 mm focal length). The pellicle beam splitter 40 reflects the light from the target path to the eyepiece 11. Both the bleaching path and the target path are monitored and controlled by monitors 43 and 55. The monitors receive a small percentage of the source light due to reflection from the glass plates 56 and 54. The monitors 43 and 55 are photodetectors that are feedback components of closed loop control systems for each of the LED sources 41 and 53. Light from the LED 41 may be delivered to the eye 10 as a single pulse or as multiple pulses. In using the system of FIG. 2, the LED 53 and aspheric lens 52 may be initially adjusted to produce an image of the LED 53 at the lens 45. The target 50 may then be moved to produce a demagnified image at the input to the eyepiece 11. The LED 41 and aspheric lens 42 are then adjusted to produce an image of the LED 41 at about the eye pupil plane. Separate amplifier/feedback and drive signals are preferably used for the target and bleach LED control. The target LED 53 may also be pulsed if desired.

The light entering the eye bleaches the visual pigments to various levels as a function of the brightness, duration, and number of pulses of light. Generally, the LED 41 is utilized to bleach the visual pigments to a deep bleach. Return to visual acuity is determined by providing a target image 50 that is illuminated by the LED 53. The illumination level on the target is at a low level, and it may be either a constant or flickering illumination. In this embodiment of the invention, the observer pushes a button switch 22, which provides an electrical signal to the data analysis system 17 at the point in time when the observer is able to identify the particular visual entity of the target (the time corresponding to the return of a critical amount of regenerated visual pigment). The data analysis system 17 then records the time from cessation of the bleaching signal to the time when the patient is able to identify the particular visual entity (either a constant visual target or a flickering target). By measuring the time to return of visual acuity after an intense bleach, the rate of photopigment regeneration is determined. At higher levels of glucose, regeneration is faster and, therefore, time to return to visual acuity is reduced. By characterizing a patient's return to visual acuity at various glucose levels, a profile is established that allows glucose concentration to be calculated based on return to visual acuity after a known degree of bleaching.

FIG. 3 is a depiction of one example of the time varying intensity of the illumination source used to bleach the visual pigments of the retina. The time varying signal is preferably a pulsed signal as shown in FIG. 3. Following the bleaching signal, which in the preferred embodiment is a 1–6 Hz signal that lasts for a total of 1–5 seconds, a target is presented to test the return of visual function. The wavelength of the illuminating (bleaching) light is preferably in the range of 500 nm to 650 nm, e.g., 595 nm, for analysis of glucose, although other wavelength ranges may be utilized as appropriate. Alternatively, the bleaching light may be a single pulse of light of a selected duration.

Figure 4:
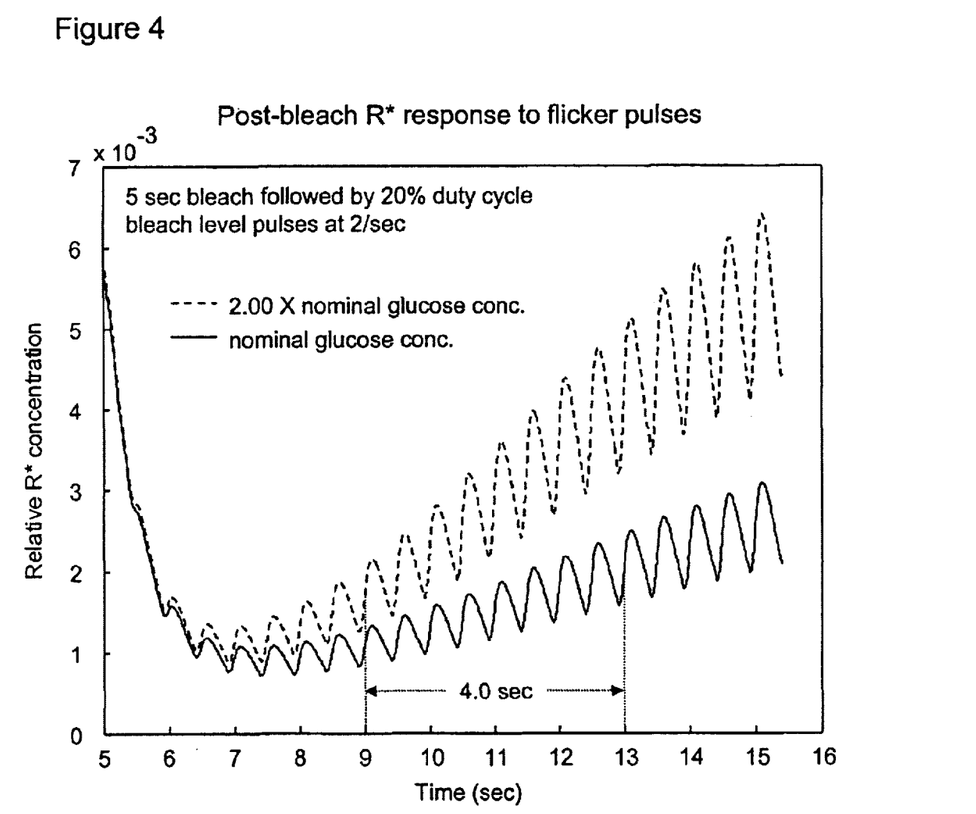
FIG. 4 is a graph illustrating the results of a mathematical simulation of the time response of the activated visual pigment concentration for two different glucose concentrations using flicker recognition testing, following bleaching of the retina.

FIG. 4 shows the results of a computer implemented mathematical simulation of concentrations of $R^*$, activated rhodopsin, versus time (in seconds), for two different blood glucose concentrations following retinal bleaching. On this graph, the baseline blood glucose is depicted as well as a concentration of two times the baseline glucose concentration. Time is displayed on the abscissa (in seconds) while the ordinate depicts the relative concentrations of activated rhodopsin. Prior to the time zero on the abscissa, a bleach has been performed, followed by a visual acuity test using a flickering target to test the return of visual function. The flickering light, flickered at a rate of 2 Hz, with a 20% duty ratio was projected onto the retina at an intensity of $\frac{1}{10}$ of the bleaching intensity. The change in concentration of $R^*$, activated rhodopsin, with each flicker is noted as fluctuations in the curves. The effect of different glucose levels on the rate of rhodopsin regeneration can be determined from FIG. 4 as follows: The point in time when enough rhodopsin has been generated to allow the observer to "see" the flickering light is represented by the points labeled 1 and 2 on the graph. Those points have equal relative excursions of R* concentration. The time difference between points 1 and 2 on the graph is 4.0 seconds. This means that as the observer's glucose level changes by a factor of 2, the time required for the observer to first see the flickering source is reduced by 4.0 seconds.

Figure 7:
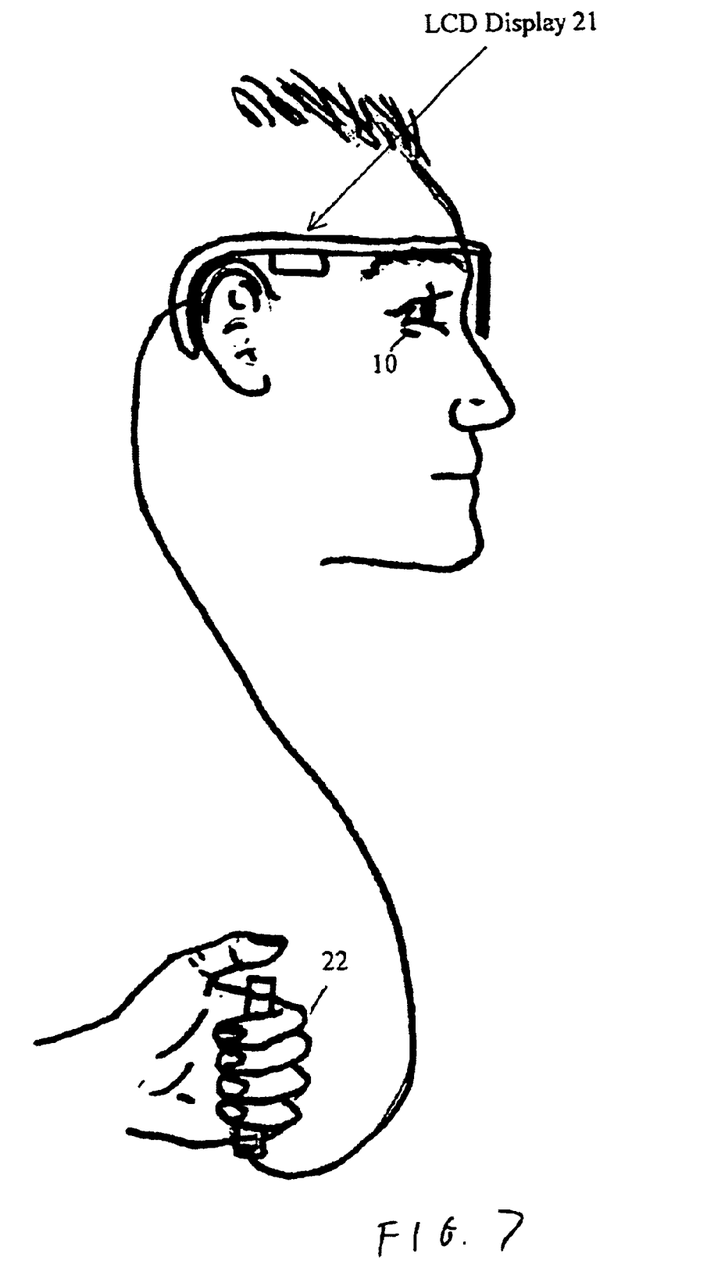
FIG. 7 is a schematic side view of a measurement device that may be utilized in accordance with the invention.

An illustration of an exemplary device embodying the invention is shown in FIG. 7. This unit contains the elements depicted in FIG. 1 and FIG. 2. This device may be similar to commonly marketed virtual-reality glasses. The display 21 provides the glucose concentration information to the patient, preferably utilizing an LCD screen. A button 22 is provided to both activate the unit, in a manner similar to taking a photograph with a standard camera, and to signal the return of the ability to recognize the visual signal following bleaching. The unit is preferably self-contained and contains batteries and memory.

The second embodiment of the invention utilizes a system of color-matching to measure visual pigment regeneration and therefore derive blood glucose concentration values. The use of color-matching tests to determine the rate of visual pigment regeneration after bleaching is described in detail by Burns et al. in A Psychophysical Technique for Measuring Cone Photopigment Bleaching, Invest. Ophthal. Vis. Science, 28:711–717, 1987, and by Wyszecki in Color-matching at Moderate to High Levels of Retinal Illuminance: A Pilot Study, Vision Res. 18: 341–346, 1978, which are herein incorporated by reference. By measuring the rate of regeneration of the visual pigment, the concentration of blood glucose can be accurately predicted.

Figure 8:
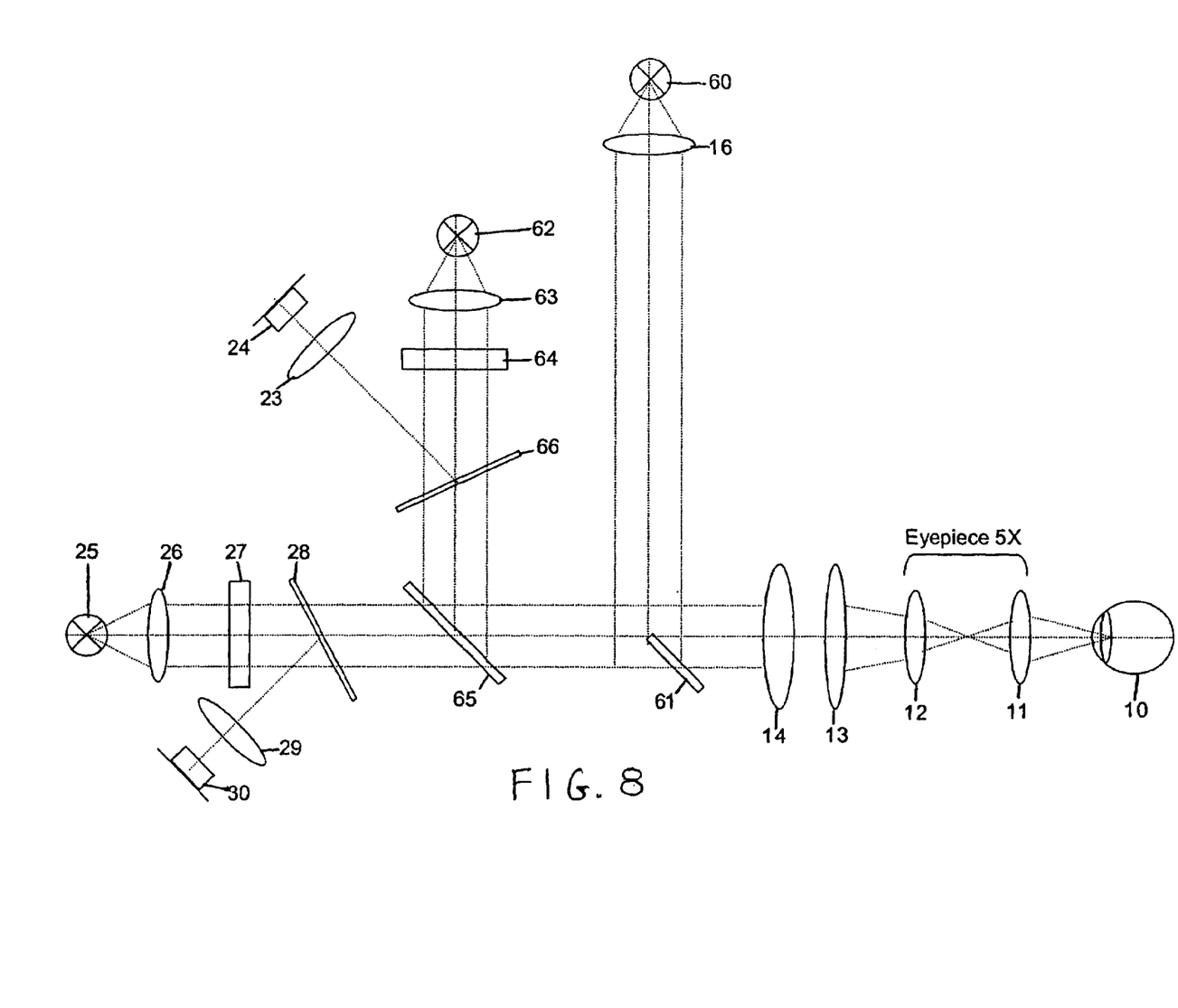
FIG. 8 is a schematic diagram of the apparatus for measurement of blood glucose concentration utilizing color-matching tests.

With reference to FIG. 8, an optics system for use in conjunction with the second embodiment will be described. A three light source optical system is utilized to psychometrically assess the cone pigment regeneration rate of a patient with eye 10. A first light source 60 is an LED with yellow color at a nominal wavelength of 595 nm. The light from the source 60 is collimated with an aspheric lens 16 and directed to the patient's eye 10 via a biparte mirror 61 and lens combination 13 and 14 and finally an eyepiece lens combination 11 and 12. The mirror 61 splits a field such that the light from the yellow source 60 occupies one half of the field and the combination of the light sources 62 and 25 occupies the other half of the field as seen by the patient's eye 10. The light source 62 may be a white LED, which is collimated by an aspheric lens 63 and filtered by a green filter 64 passing light at nominal 550 nm. The light source 25 may be a white LED used in conjunction with a red filter 27, or a red LED without a filter. An aspheric lens 26 is employed in the red path. The red and green paths are combined with a dichroic beam splitter 65. This beam splitter efficiently passes red and reflects green. Both red and green paths employ pick-off glass plates 66 and 28 that direct a small portion of the light from the sources 25 and 62 to photodetectors 30 and 24. Focusing lenses 29 and 23 are used to image the respective LED onto its photodetector. The photodetector arrangements are used to control and stabilize the light from the red and green paths via feedback circuitry.

The optical apparatus of FIG. 8 is controlled by the electrical system depicted in FIG. 9. The light intensity level of the yellow LED 60 is controlled by a controller and data analysis system 31 to step through a sequence of light intensities from low to high. A series of color and intensity matches are performed by observing the two halves of light provided by the optical system to the patient's eye 10. The yellow light starts at a low illumination level; the observer adjusts the red and green balance knob on a control interface box 32 to obtain a color-match, and then the observer adjusts the intensity knob I to obtain an intensity match. It may be necessary for the observer to move back and forth from the red/green balance to the intensity several times to obtain the best match. When the observer is satisfied that a best match has been obtained, the observer pushes a switch S which signals the controller 31 that a match has been made. The controller logs the yellow, red, and green drive voltage levels at that time, and then advances the level of yellow to the next level, whereupon the matching process is repeated. For a full range analysis, matches may be performed for about 8 intensity levels of yellow. Alternatively, a final configuration of the color-match test may contain only one or a few matches. This is made possible by establishing a calibration curve for each patient which will be stored in the data storage 18.

Figure 10:
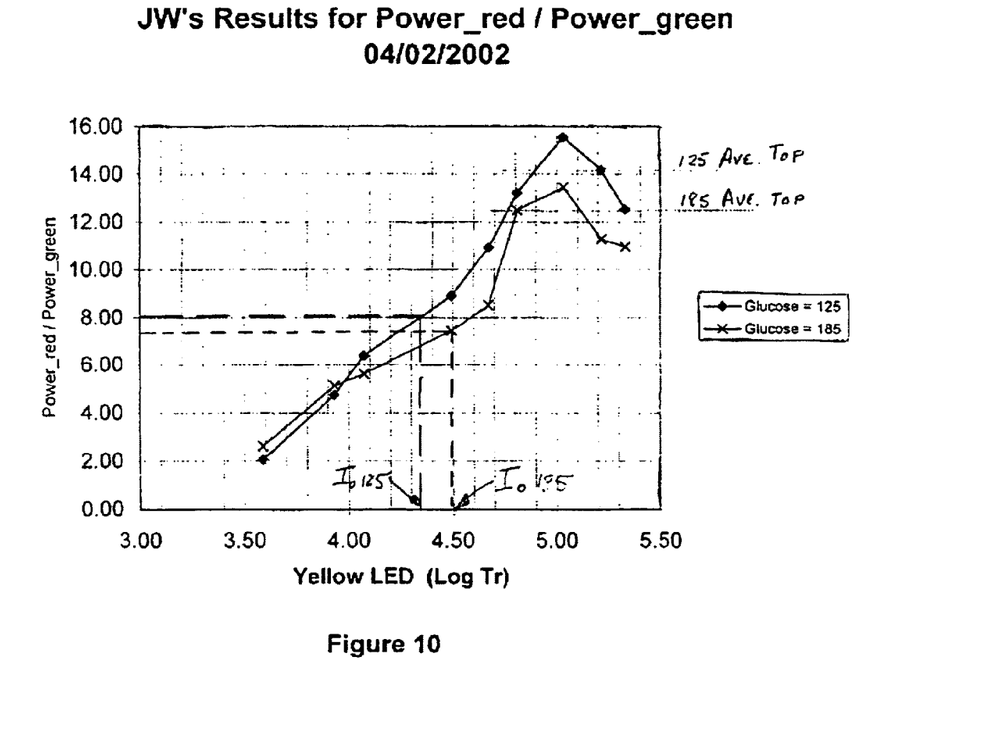
FIG. 10 is a graph of actual patient data obtained from the color-matching device of FIG. 8 showing the change in color-matching curves (illumination in Log Trolands vs. red/green power ratio) with two different blood glucose concentrations.

It is well known that the rate of regeneration of cone color pigment causes the curve of red/green illumination vs. yellow illumination to shift to the right, or to higher yellow illumination (Burns, et al., A Psychophysical Technique for Measuring Cone Photopigment Bleaching, Invest. Ophthalmol. Vis. Sci. 28:711, 1987). By defining a red to green ratio at which to assess the illumination level of yellow, i.e. $I_o$, a correlation can be made which relates glucose level to the shift in illumination of yellow at $I_o$. FIG. 10 shows an example of the relationship of red/green vs. yellow intensity in log Trolands (Tr). The yellow light level is indicated at two levels of glucose. The controller 31 contains the analysis firmware to determine the glucose level based on the yellow illumination value at $I_o$. This information is stored in "Data History Log" and is displayed by the display system 21. The value displayed on the display system 21 is utilized by the patient to take the necessary action on glucose management. On a regular basis, such as a 3 to 6 month interval, a care provider may analyze the "Data History Log". If necessary, a new calibration curve can be determined by the care provider and loaded into the controller 31. The measurement device will also be reactivated for another 3 to 6 months of use; thus encouraging the patient to return to the care provider for consultation.

The invention is described in more detail in the following non-limiting examples.

EXAMPLES

Example 1

Figure 5:
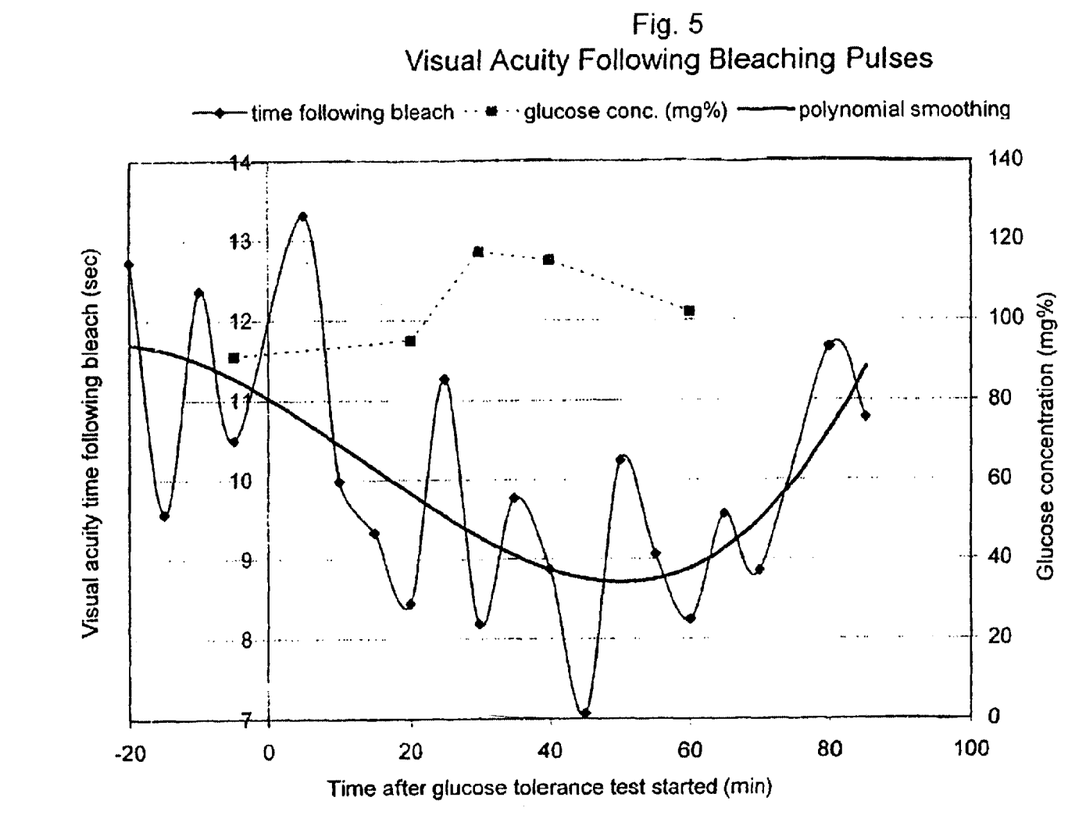
FIG. 5 is a graph of actual patient data showing the change in the rhodopsin regeneration rate as measured by the time following a bleach plotted during glucose tolerance testing over a period of 95 minutes. Also plotted on this graph are the blood glucose concentrations measured with standard invasive whole blood glucose testing procedures.

Visual Acuity Test: Effect of Increasing Glucose Concentration on Pigment Regeneration FIG. 5 is a graph of actual patient data showing the change in the rhodopsin regeneration rates as measured by the time to restoration of visual acuity (measured in seconds) following a series of bleaching pulses plotted against the time (measured in minutes) during glucose tolerance testing. The tests were conducted on the apparatus shown in FIG. 2. At time zero on the x-axis the subject completed drinking a glucose solution. The four points to the left of time zero were measured as baseline tests. Also in this graph is shown the actual blood glucose concentration as measured with a traditional blood glucose testing method (One Touch System, Lifescan, Inc. Johnson and Johnson). FIG. 5 demonstrates the correlation between increasing blood glucose levels and decreasing times to visual acuity which correspond to faster rhodopsin regeneration times.

Example 2

Figure 6:
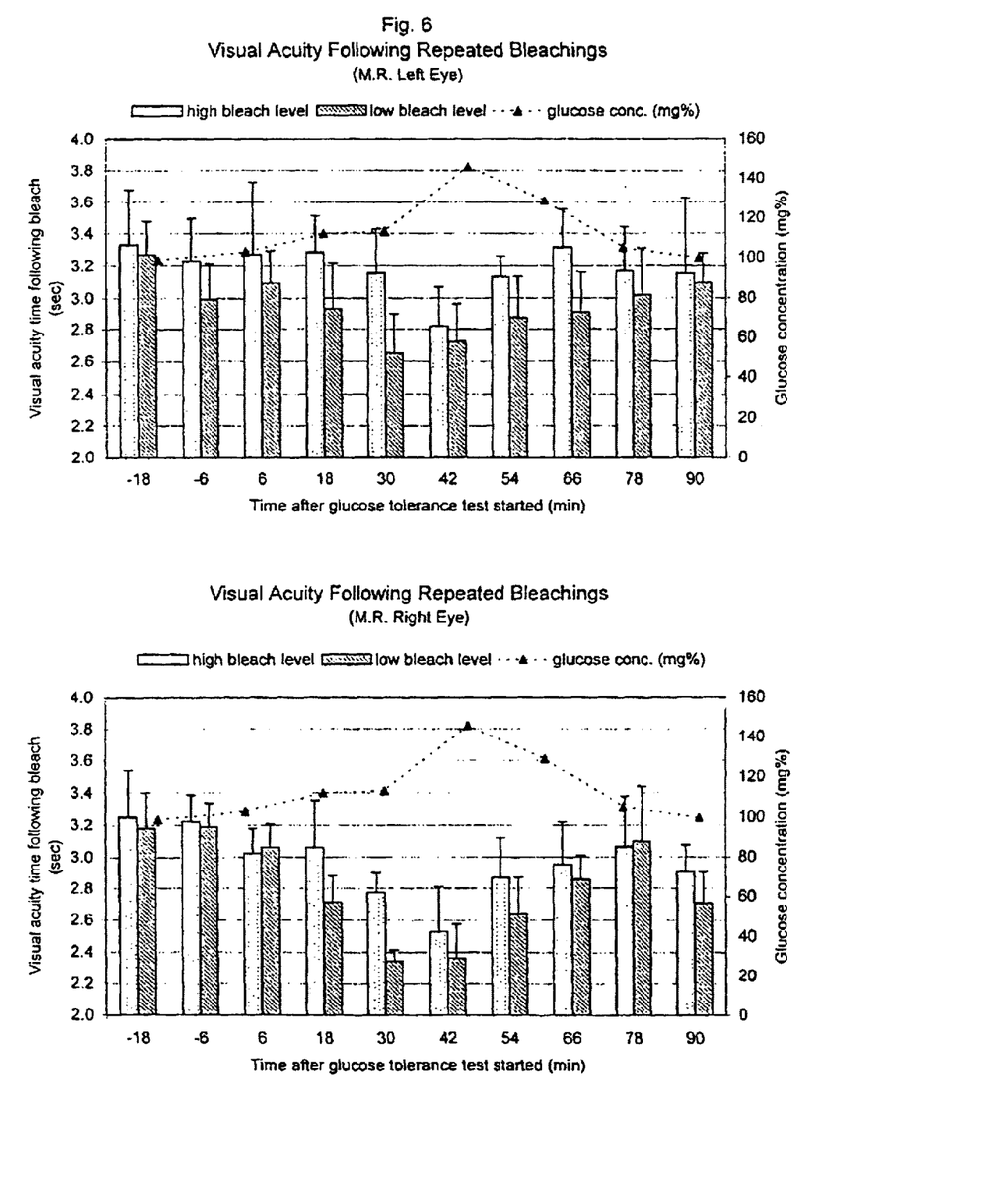
FIG. 6 is a graph of actual patient data showing the change in the rhodopsin regeneration rate as measured by the average times of return of visual acuity following repeated bleaches plotted during glucose tolerance testing over a period of 95 minutes. Also plotted on this graph are the blood glucose concentrations measured with standard invasive whole blood glucose testing procedures.

Visual Acuity Test: Effect of Increasing Glucose Concentration on Pigment Regeneration Visual acuity tests were conducted using a system wherein a single bleaching light pulse is triggered each time the patient is just able to see the visual acuity target. This process is repeated eight times and the resultant data set is a series of triggering time periods that are summated and then averaged. Longer visual pigment regeneration times produce longer average time periods. FIG. 6 shows actual patient data using this method of averaging the time periods between successive repeated bleachings. As shown in the graph, the visual pigment regeneration times decrease as the blood glucose concentration increases and the regeneration times then increase as the blood glucose values return to baseline. At time zero on the x-axis the subject completed drinking a glucose solution. The two points to the left of time zero were measured as baseline tests. At each testing point, two separate bleaching levels were used and are plotted next to each other on FIG. 6. These are referred to as "high bleach level" and "low bleach level".

Example 3

Color-matching Test: Effect of Increasing Glucose Concentration on Pigment Regeneration FIG. 10 shows actual patient data from color-matching tests. The tests were conducted at two different blood glucose concentration values. The data were obtained using the color-matching apparatus shown in FIG. 8. As shown in the graph, there is a right shift of the curve of red/green intensity versus yellow intensity and $I_o$ with a higher blood glucose concentration value. Individual patient calibration reveals a plot of $I_o$ vs. blood glucose concentration. The blood glucose can be ascertained for a patient by measuring the $I_o$ point and then calculating the appropriate blood glucose value. The desired relationship may be amenable, alternatively, to development as a look-up table, regression model, or other algorithm carried out with a special purpose computer or an appropriately programmed personal computer, work station, etc.

While preferred embodiments have been illustrated and described, it should be understood that changes and modifications can be made therein in accordance with ordinary skill in the art without departing from the invention in its broader aspects as defined in the following claims.

What is claimed is:

1. A method for determining the glucose concentration in blood comprising:
   (a) bleaching visual pigments in the retina of an observer's eye with a bleaching light;
   (b) conducting a psychophysical test that measures the observer's psychophysical response to a visual stimulus;
   (c) analyzing the psychophysical response to determine the rate of pigment regeneration; and
   (d) analyzing the rate of pigment regeneration to determine the glucose concentration in the observer's blood.

2. The method of claim 1 further comprising storing data on the observer's blood glucose concentrations over time to create a data history for the observer.

3. The method of claim 1 wherein the psychophysical test is a visual acuity test.

4. The method of claim 1 wherein the psychophysical test is a color-matching test.

5. The method of claim 1 wherein the visual pigments are selected from the group consisting of rod pigments and cone pigments.

6. The method of claim 1 wherein the bleaching light contains wavelengths in the range of 500 nm to 650 nm.

7. The method of claim 1 wherein bleaching the visual pigments comprises projecting a bleaching light through the pupil of the observer's eye onto the fundus.

8. The method of claim 1 wherein analyzing the rate of pigment regeneration comprises using a neural network simulator to determine the glucose concentration in the observer's blood.

9. The method of claim 1 wherein analyzing the rate of pigment regeneration comprises comparing the measured rate of pigment regeneration with a set of patient calibration data.

10. An apparatus for determining the concentration of glucose in blood comprising:
    (a) means for projecting a bleaching light into an eye of an observer to bleach visual pigments in the retina of the eye;
    (b) means for providing a visual stimulus to the eye of the observer;
    (c) means for analyzing the observer's psychophysical response to the visual stimulus to determine the rate of pigment regeneration; and
    (d) means for analyzing the rate of pigment regeneration to determine the concentration of glucose in the observer's blood.

11. The apparatus of claim 10 further comprising means for displaying the measured concentration of glucose in the observer's blood.

12. The apparatus of claim 10 further comprising means for storing data on the observer's blood glucose concentrations over time to create a data history for the observer.

13. The apparatus of claim 10 wherein the means for analyzing the observer's psychophysical response to a visual stimulus is a visual acuity test.

14. The apparatus of claim 10 wherein the means for analyzing the observer's psychophysical response to a visual stimulus is a color-matching test.

15. The apparatus of claim 10 wherein the bleaching light contains wavelengths in the range of 500 nm to 650 nm.

16. The apparatus of claim 10 wherein the means for providing a visual stimulus is an illuminated object.

17. The apparatus of claim 10 wherein the means for providing a visual stimulus is a flickering light.

18. The apparatus of claim 10 wherein the means for providing a visual stimulus is a field, the field separated into areas of different color and intensity.

19. The apparatus of claim 10 wherein the bleaching light has a modulated amplitude.

20. The apparatus of claim 10 wherein the bleaching light comprises a plurality of light pulses.

21. The apparatus of claim 10 wherein the means for projecting a bleaching light into an eye of an observer is a light emitting diode, a xenon lamp, or a halogen light.

22. The apparatus of claim 10 wherein the means for analyzing the rate of pigment regeneration is a neural network simulator.

* * * * *